United States Patent [19]

Marty et al.

[11] 4,231,864
[45] Nov. 4, 1980

[54] PROCESS FOR PREPARATION OF A WATER FOR HEMODIALYSIS, AND ITS APPLICATION IN RENAL HEMODIALYSIS

[76] Inventors: Didier Marty, 6, rue Clémence Isaure, 31000 Toulouse; Albert Abadie, 18, rue de Nimes, 31400 Toulouse; Michel Mustin, 8, rue du Libre Echange, 31000 Toulouse, all of France

[21] Appl. No.: 945,296

[22] Filed: Sep. 25, 1978

[30] Foreign Application Priority Data

Oct. 21, 1977 [FR] France .................. 77 32009

[51] Int. Cl.³ .............................. B01D 15/04
[52] U.S. Cl. .................. 210/669; 210/673; 210/678; 210/683; 210/927
[58] Field of Search .......... 210/22 R, 22 A, 22 C, 210/22 D, 27, 30 R, 32, 34, 35, 37 R, 38 A, 96 M, 259, 321 R, 321 A, 321 B; 562/607, 608

[56] References Cited

U.S. PATENT DOCUMENTS

| | | | |
|---|---|---|---|
| 2,697,725 | 12/1954 | Bryce | 210/37 R |
| 3,515,275 | 6/1970 | Bowman | 210/22 |
| 3,843,566 | 10/1974 | Barrett | 210/37 R |
| 3,962,075 | 6/1976 | Fialkoff et al. | 210/22 C |

OTHER PUBLICATIONS

Dorfner, K. *Ion Exchangers, Properties and Applications* Mich., Ann Arbor Science, 1972, pp. 18-20 & 102.

*Primary Examiner*—Ivars C. Cintins
*Attorney, Agent, or Firm*—Shlesinger, Arkwright, Garvey and Dinsmore

[57] ABSTRACT

The invention concerns a process for preparation of a water for hemodialysis, particularly renal hemodialysis, and consists of fixing the acetate anions ($CH_3COO^-$) on at least one water-insoluble anion-exchange resin contained in a column and passing a potable water through a bed of said resin which is thus prepared, in order to substitute the anions contained in the initial potable water for the acetate anions. The water which is obtained is devoid of ions which are undesirable for the hemodialysis process and is suitable for the preparation of a hemodialysis solution by means of a traditional type of aqueous solution.

12 Claims, 3 Drawing Figures

PROCESS FOR PREPARATION OF A WATER FOR HEMODIALYSIS, AND ITS APPLICATION IN RENAL HEMODIALYSIS

The invention concerns a process for preparation of a water for hemodialysis; it extends to the water which is obtained and to its application in the field of renal hemodialysis.

Until this time, renal hemodialysis solutions are most frequently prepared from public potable water, after softening, if only hard water is available.

In some rare installations, treatments are realized which are intended to eliminate the various salts from the water, particularly reverse osmosis, distillation, or ion-exhange demineralization treatments.

These treatments exhibit all of the inconveniences in obtaining a specific water for hemodialysis. For example, the reverse osmosis treatments are insufficient in effect and allow an "ion leak" which is incompatible with the ionic composition norms which the hemodialysis waters must maintain. Also, this type of treatment is very burdensome both in investment and in operation.

The distillation treatments produce a water of very good quality, but the cost, particularly because of energy consumption, is even greater than that of reverse osmosis, which negates any practical possibility of using them to obtain hemodialysis waters.

The known ion-exchange demineralization treatments consist, on the one hand, in a resin which is in the acid form $R-H^+$ of exchanging the $H^+$ with cations which are present in the water, and on the other hand, in a resin which is in the hydroxide form of $R-OH^-$, of exchanging the $OH^-$ and $H^+$ ions are reacted to produce water, either by mixing the resins in a common bed (mixed bed treatment), or by passing the water successively through the resins in two separate beds (separate beds treatment). These processes in mixed bed or separate beds present the inconvenience of producing a water which is very corrosive to the various metallic parts which come in contact with it. Moreover, the treatment in mixed bed exhibits a very grave shortcoming arising from the resin regeneration operations, operations which are very delicate and cannot generally be effected except periodically in specialized facilities. Furthermore, the treatment in separate beds presents the inconvenience of producing a water which is not neutral and necessitates a supplementary neutralizing treatment. Additionally, in separate beds, the regeneration of each of the bed requires handling of concentrated acidic and basic solutions, and such handling in a medical milieu is dangerous, and totally prohibits use of the process in the home of the patient, while it can be used in a well equipped hospital only with multiple controls.

The present invention remedies the inconvenience of the known processes with a new process for preparation of water for hemodialysis produced by ion exchange.

One particular object of the invention is to obtain a noncorrosive hemodialysis water, of which the salinity arises almost exclusively from ions which are tolerated, and even sought in hemodialyses, and which totally satisfy the prescribed standards.

Another object is the simple regeneration of the base products, which can be effected at any site and with total safety in the home of the patient as well as in the hospital.

For this, the process of the invention for preparation of a water for hemodialysis consists of fixing acetate anions $CH_3COO^-$ on at least one water insoluble anion-exhange resin, and passing a potable water through a bed of said prepared resin in order to substitute the anions contained in the initial potable water for the acetate anions.

Studies and tests on this process have required the cooperation of three specialities: medical technology to define the optimum conditions to be satisfied by the water which is obtained, hydrology technology to analyze the natural deficiencies of the potable waters which are presently used, deficiencies which are exaggerated as a function of the qualities required by hemodialysis, and finally, chemical technology to assure the practical elimination of undesirable constituents and to obtain water of suitable quality. These studies and tests which are realized with the cooperation of specialists of the three specialties led to the discovery of an anion having a remarkable power of substitution of the undesired ions, which anion is not only tolerated, but actually desired in hemodialysis, since it constitutes one of the important components of the hemodialysis solution which is realized from the water. The process, as used with this $CH_3COO^-$ anion, consists of fixing this anion on a resin in order to effect the substitution of the undesired anions which are present in the initial water: nitrates, fluorides, sulfates, chlorides, phosphates, and also carbonates and bicarbonates and sometimes nitrites.

It is confirmed that in this process there are almost no ionic leaks observed, particularly of these undesired ions. In other words, they remain below the detection threshholds of current analytical technology, and the water which is obtained is of perfect quality for hemodialysis.

Also, the salinity furnished by the acetate which has been substituted for these undesired ions furnishes a slightly basis pH to the water, so that it has no corrosive character. For an even very saline initial water, the concentration of acetate ions which is introduced in the water by the process is in every case lower than the final concentration sought for the hemodialysis solution, so that no subsequent treatment is necessary, and the aqueous hemodialysis solution can be mixed directly in the water which is obtained.

Moreover, the process of the invention eliminates the $CO_3^=$ anions which are substituted by the acetate anion; thus, the parasitic precipitation of the carbonates, which could intervene, is avoided when the alkaline earth cation-rich aqueous hemodialysis solution is mixed with water.

Also, the elimination of the $CO_3H^-$ anions is produced under the effect of the heat, according to the following reaction:

$$2CO_3H^- \rightarrow CO_3^{--} + CO_2 + H_2O$$

If the initial potable water is very soft, the preparation process is carried out directly from the water. On the contrary, if an initial water has a hydrotimetric level about 0.5° TH (French unit), the process includes the complementary traditional softening phase, to lower the TH level to a negligible value. This softening can be realized by means of suitable ion-exchange resins, either beforehand in a separate apparatus, or in the same apparatus which is then provided with two categories of resins.

Various anion-exchange resins, either as is or after proton addition, are commercially available and capable of fixing the acetate ion for its subsequent substitution. For example, the following resins give very good results, as strongly basic resins:

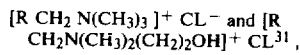
[R CH$_2$ N(CH$_3$)$_3$ ]$^+$ CL$^-$ and [R CH$_2$N(CH$_3$)$_2$(CH$_2$)$_2$OH]$^+$ CL$^{31}$, wherein R is an organic polymer group. The fixing of the acetate anion is effected by passage of a concentrated metallic acetate solution, particularly alkaline, to provide resins in acetate form, of the following formula:

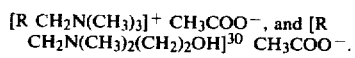
[R CH$_2$N(CH$_3$)$_3$]$^+$ CH$_3$COO$^-$, and [R CH$_2$N(CH$_3$)$_2$(CH$_2$)$_2$OH]$^{30}$ CH$_3$COO$^-$.

In the case where the initial potable water may contain pollution by organic materials, the base resins are, at least partially, macroporous resins which include positive quaternary ammonium sites. Thus, the humic acid, detergent or the like type of pollutants are retained by the resin.

The resin or resins used are preferably granular resins arranged in a compact filtering bed, so as to also retain the impurities in suspension which might be in the water.

The regeneration of the resin or resins can be realized very simply in most cases, particularly for the strongly basic resins, by passage of a concentrated solution of a metallic acetate which is particularly alkaline through the bed; the process can be carried out periodically by generating a succession of cycles each comprising an exchange phase to furnish the water for hemodialysis and a regeneration phase. This type of traditional process can be effected by means of an apparatus known to those skilled in ion-exchange technology. It is to be noted that this regeneration leads to handling of the components without danger and can be realized within these devices without particular precaution by manual, semi-automatic or automatic means, and in the home of the patient as well as in the hospital.

It is also to be noted that for some middle or low basic resins, for example R N(R')$_2$ or R NH(R'), wherein R' is an organic group, the best regeneration consists of passing first a concentrated base solution, then an acetic acid solution successively through the resin. In this case, it is preferable to carry out this type of regeneration in a hospital milieu, and for hemodialysis in the home of a patient, other types of resins are preferred.

Various tests have shown that the optimum conditions for carrying out the process were essentially the following:
- flow passage of the water through the resin bed at the most equal to approximately 40 volumes of water per volume of resin per hour;
- temperature between approximately 5° C. and 40° C.;
- water pressure below approximately 6 kg/cm$^2$.

Beyond these limits, it is possible either to observe slight ionic leaks from too great a flow, or to be obliged to provide a cooling of the water if the temperature is too high, or to observe a premature mechanical wear of the resins by crushing if the pressure is too high. The bottom temperature is determined by considerations of the kinetics of exchange and practical considerations, such as risk of freezing, etc.

As the process of the invention has been disclosed in its general form, the following description furnishes an example of a test with a potable water which is artificially doped with fluoride ions and nitrate ions, in Example 1, and an illustrative example of carrying out the process, in Example 2, and an example of clinical application of the water obtained by the process, in Example 3.

The attached drawings are intended to facilitate understanding of these examples.

EXAMPLE 1

Figure 1:
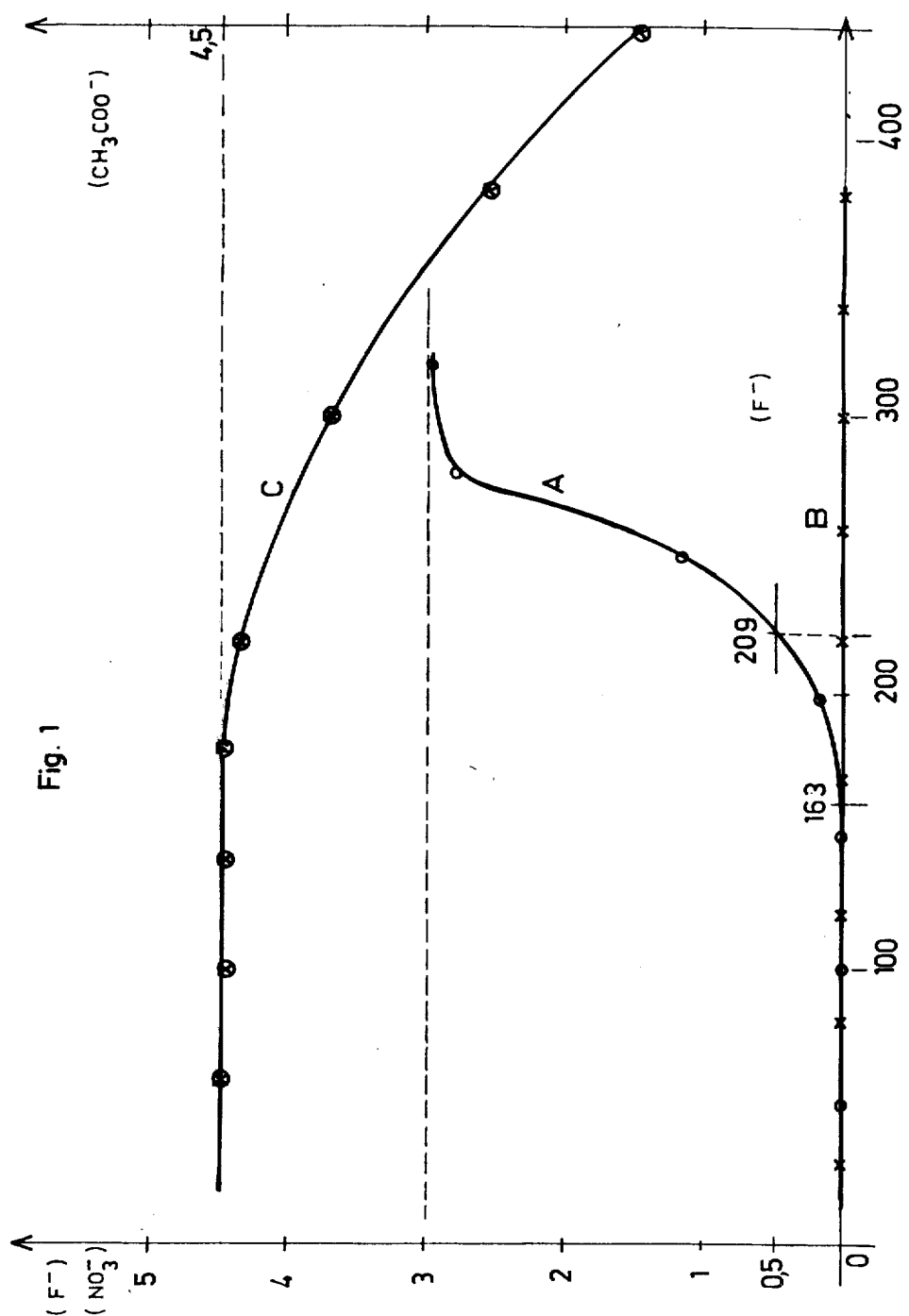
FIG. 1 shows the curves A, B, C obtained in the course of Example 1.

The few existing processes for preparation of water for hemodialysis are mostly inefficient for the elimination of fluoride anions and, to a lesser extent, the nitrate anions which are, with the nitrite anions, very undesirable for hemodialysis. It is to be noted that, in principle, a potable water has no nitrite anions.

This test is intended to illustrate the total efficiency of the process according to the invention for elimination of these fluoride and nitrate anions in all practical cases of initial potable water which is likely to be used.

For this test, a natural water with total salinity before doping which was equal to 4.1 milliequivalent per liter, abbreviation mE/l, was strongly doped 3 milligrams/liter of fluoride ions in the form of sodium fluoride and 15.5 milligrams.liter of nitrate ions in the form of sodium nitrate.

The resin used is a Duolite resin A 101 D manufactured by "Dia Prosim," of the formula: [R CH$_2$N(CH$_3$)$_3$]$^+$Cl$^-$; this resin, which is obtained by organic synthesis, is subjected to strong acid washing, for example with hydrochloric acid, and/or a solvent, for example methanol, so as to eliminate the basic components which have not reacted.

The washed resin is arranged in a compact stationary bed in a column and a concentrated sodium acetate solution is passed through it for approximately 45 minutes to totally substitute the CH$_3$COO$^-$ anions for the Cl$^-$ anions.

The aforementioned doped water is passed through the prepared resin: [R CH$_2$N(CH$_3$)$_3$+[$^{CH}$$_3$COO]$^-$, of which the volume in the column is equal to eleven liters, and the concentration of fluoride, nitrate, and acetate at the discharge is periodically removed.

The curve A is the curve of fluoride ion leakage as the abscissus records the volumes of water passed through relative to one liter of resin. It is established that the fluoride ion leakage is absolutely zero up to 163 liters of water per liter of resin; and between 163 and 209 liters of water per liter of resin, the fluoride concentration remains below the tolerable threshhold for hemodialysis. It is thus obvious that the fluoride ions are very well retained, even in the extreme case of a very strongly doped water, on the order of ten times more concentrated than the most concentrated waters which might be used in practice.

The curve B is analogous to curve A, but is for the nitrate anions. Here too it is established that these anions are very well retained up to at least 380 liters of water per liter of resin. The curve is merged with the axis of the abscissa.

The curve C represents the total concentration of acetate upon discharge and shows that all of the original anionic salinity, 4.1 mE/l of natural salinity, plus 0.15 mE/l of fluoride doping and 0.25 mE/l of nitrate doping, is substituted integrally with acetate anions up to 180 liters of water per liter of resin, which is precisely the object of the process, since the acetate anion is a desired component in hemodialysis.

EXAMPLE 2

Figure 2:
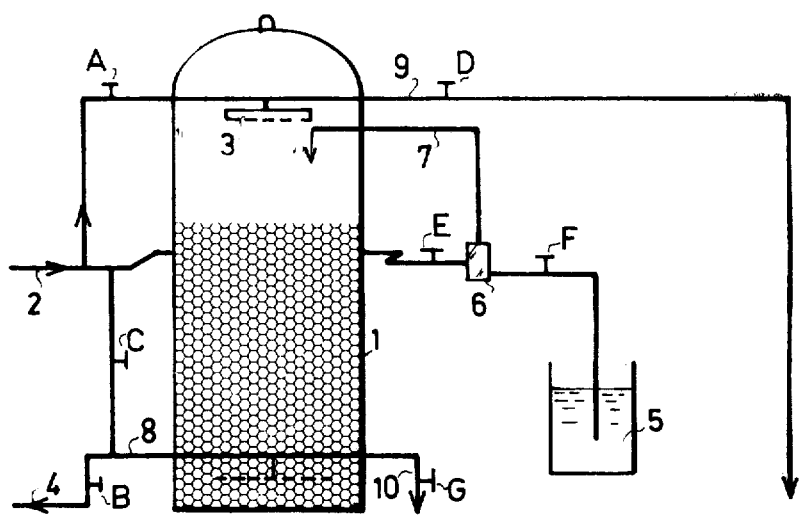
FIG. 2 shows a schematic diagram of an apparatus as used in Example 2.
Figure 3:
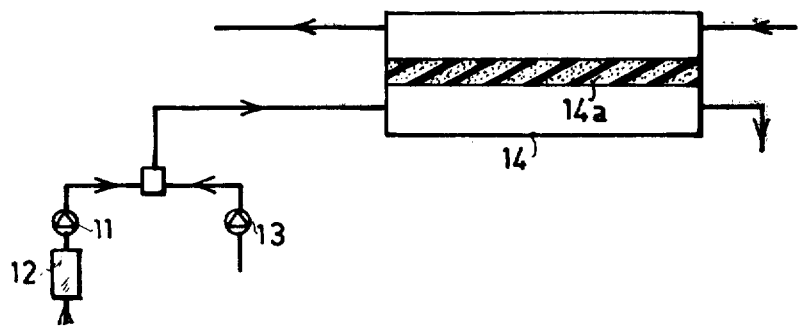
FIG. 3 is a symbolic diagram of an artificial kidney using a hemodialysis water of the type obtained in Example 2.

This example illustrates, in reference to FIG. 2, the process as carried out in a real practical circumstance.

The resin used is washed beforehand as in the preceding example, and is of the following type, after fixation of the acetate ion:

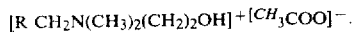

$[R\ CH_2N(CH_3)_2(CH_2)_2OH]^+[CH_3COO]^-$.

Eleven liters of resin are placed in a compact bed in column 1, of which approximately the top third is left free.

The initial potable water is city water from the public reservoir of Toulouse, of which the characteristics are the following:
pH=7.6
conductivity: 285 micro ohm/cm
total hardness: 13.5 TH (French unit)
fluoride: mean concentration 0.6 milligram/l
nitrate: 5 mg/l
chloride: 10 mg/l
nitrite: imperceptible
sulfate: 15 mg/l
T.A.C. (Complete Alkalimetric Mark): 10° French
iron: 0.05 mg/l
ammonium: below 0.05 mg/l This water is softened beforehand on a sulfonic ion-exchange resin, functioning in initial sodium form, and its total hardness is decreased to a negligible value.

The softened water is passed at a flow rate of 33 liters/hour by a passage a through a strainer 3 to the top of column 1; this flow corresponds to 3 volumes of water per volume of resin and per hour. The water temperature is on the order of 20° C. and its pressure on the order of 4 kg/cm$^2$.

The hemodialysis water is discharged through a passage 4 and has the following composition:
fluoride: imperceptible
nitrate: imperceptible
nitrite: imperceptible
sulfate: imperceptible
chloride: imperceptible
acetate: 2/55 mE/l The water is perfect for hemodialysis since all of the undesired ions are eliminated. It retains the same properties for approximately 110 hours of use which nearly corresponds to sixteen dialysis sessions.

In practice, the regeneration is effected at the end of approximately ninety hours of use to satisfy a traditional safety coefficient in the medical practice.

The regeneration begins by clearing the bed by passage of a countercurrent of water through a passage 8 with discharge of the clearing water through strainer 3 and evacuation passage 9 to the drain; this clearing stage lasts about ten minutes.

The regeneration itself is then effected with a concentrated sodium acetate solution which is aspirated from a tank 5 through a Venturi 6 to provide a diluted solution which is introduced through a passage 7 into the column. In the traditional manner, faucets A to G on the passage are for the various desired connections. This solution is passed through for approximately forty minutes. After passing through the column, the effluent is evacuated toward the drain through a passage 10.

This regeneration operation is followed by a rinsing stage by co-current passage of water, arriving through strainer 3 and leaving through passage 10; this rinsing lasts approximately twenty minutes.

The exchange phase can then take place. The quantity of regenerant used for the regeneration is on the order of 0.7 kg of trihydrated sodium acetate per liter of resin, which is not very costly.

Of course, other installations can be used to carry out the process, particularly semi-automatic or automatic installations wherein the regeneration is not manually controlled, but is automatic.

EXAMPLE 3

This example illustrates a renal hemodialysis process using a hemodialysis water of the type obtained in Example 2.

The water for hemodialysis, drawn by a centrifugal pump 11, passes through a heater 12 before being mixed with an aqueous concentrated hemodialysis solution which is drawn by a peristaltic pump 13.

The aqueous solution is mixed with the hemodialysis water so that, considering the acetate ion content of the hemodialysis water, the acetate ion content of the solution remains below approximately 45 mE/l.

In the case of use of the hemodialysis water described in Example 2, the aqueous solution can have the following composition:
NaCl: 210.68 g/l
MgCl$_2$, 6 H$_2$O: 5.24 g/l
CH$_3$COO Na, 3 H$_2$O: 166.70 g/l
CaCl$_2$, 6 H$_2$O: 13.42 g/l.

This aqueous solution is diluted thirty-five times in the hemodialysis water and the solution which is obtained is passed in the customary manner into an artificial kidney 14 which in the example has a dialysis membrane 14a.

While this invention has been described as having a preferred design, it will be understood that it is capable of further modification. This application, is therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What is claimed is:

1. A process for preparation of water for hemodialysis comprising fixing acetate anions CH$_3$COO$^-$ on at least one water insoluble anion-exchange resin and passing potable water containing undesirable anions through a bed of the thus prepared resin and substituting the undesirable anions contained in the initial potable water for the acetate ions fixed on said resin, and using the acetate containing water in a hemodialysis process.

2. A process as in claim 1 wherein said initial potable water has a hydrotimetric level of about 0.5° TH and subjecting said initial potable water to a water softening step prior to passage through said bed.

3. A process as in claim 1 wherein said initial potable water contains organic materials, and wherein said anion-exchange resin comprises at least in part a macroporous resin having positive quarternary ammonium sites.

4. A process as in claim 1, 2, or 3 wherein said resin comprises a strong anionic resin, of the following formula, after said acetate anion fixing step: $[R\ CH_2N(CH_3)_3]^+[CH_3COO]^-$, wherein R is an organic polymer group.

5. A process as in one of the claims 1, 2, or 3 wherein said resin comprises a strong anionic resin, of the following formula, after said acetate anion fixing step: $[R\ CH_2N(CH_3)_2(CH_2)_2OH]^+[CH_3COO]^-$, wherein R is an organic polymer group.

6. A process as in claim 1 wherein said initial potable water contains impurities in suspension, and wherein said resin comprises a granular resin in a compact filtering bed.

7. A process as in claim 1, 2, 3 or 6 and including carrying out said preparation periodically by generation of a succession of cycles, each of which includes an exchange phase wherein said initial potable water is passed through said bed and a regeneration phase wherein a concentrated solution of an alkaline metal acetate is passed through said bed for regenerating the resin therein.

8. A process as in claim 7 wherein said resin is in a compact bed and including cleaning said bed prior to each regeneration phase by:
  (a) passing water through said bed in a direction opposite to the direction of flow of said initial potable water through said bed and thereafter
  (b) rinsing said bed by passing water therethrough in the same direction as the direction of flow of said initial potable water.

9. A process as in claim 1, 2, 3 or 6 wherein said resin comprises a medium to low basic resin and including carrying out said preparation periodically by generation of a succession of cycles, each of which includes an exchange phase wherein said initial potable water is passed through said bed and a regeneration phase comprising sequentially passing a concentrated basic solution followed by an acetic acid solution through said bed for regenerating the resin therein.

10. A process as in claim 9 and wherein said resin is in a compact bed and including cleaning said bed prior to each regeneration phase by:
  (a) passing water through said bed in a direction opposite to the direction of flow of said initial potable water through said bed and thereafter
  (b) rinsing said bed by passing water therethrough in the same direction of flow of said initial potable water.

11. A process as in claim 1, 2, 3 or 6 wherein said anion-exchange resin is produced by organic synthesis and subjecting said resin, prior to use, to a washing with a material selected from the group consisting of strong acids and solvents for eliminating unreacted basic components from said resin.

12. A process as in claim 1, 2, 3 or 6 and including passing said initial potable water through said bed at a rate of no more than 40 volumes of water per volume of resin per hour, and at a temperature between about 5° C. and about 40° C. and a pressure of less than about 6 kg/cm$^2$.

* * * * *